(12) United States Patent
Fan et al.

(10) Patent No.: US 9,334,474 B2
(45) Date of Patent: *May 10, 2016

(54) METHOD FOR MANUFACTURING CULTURE MEDIUM COMPRISING CARBON NANOTUBES AND GROWING CELLS THEREON

(75) Inventors: Li Fan, Beijing (CN); Chen Feng, Beijing (CN); Wen-Mei Zhao, Beijing (CN)

(73) Assignees: Tsinghua University, Beijing (CN); HON HAI PRECISION INDUSTRY CO., LTD., New Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/450,648

(22) Filed: Apr. 19, 2012

(65) Prior Publication Data
US 2012/0270320 A1 Oct. 25, 2012

(51) Int. Cl.
C12N 5/071 (2010.01)
C12N 5/00 (2006.01)
B82Y 5/00 (2011.01)

(52) U.S. Cl.
CPC .............. C12N 5/0068 (2013.01); *B82Y 5/00* (2013.01); *C12N 2533/10* (2013.01)

(58) Field of Classification Search
CPC ..... C12N 5/0068; C12N 2533/10; B82Y 5/00
See application file for complete search history.

(56) References Cited

U.S. PATENT DOCUMENTS

| | | | |
|---|---|---|---|
| 2005/0181143 A1* | 8/2005 | Zhang et al. | 427/532 |
| 2006/0263878 A1* | 11/2006 | Mochitate | 435/366 |
| 2007/0110741 A1 | 5/2007 | Geckeler et al. | |
| 2008/0170982 A1* | 7/2008 | Zhang et al. | 423/447.3 |
| 2009/0160796 A1* | 6/2009 | Jiang et al. | 345/173 |
| 2009/0198117 A1* | 8/2009 | Cooper et al. | 600/347 |
| 2010/0124622 A1 | 5/2010 | Wang et al. | |
| 2010/0144004 A1 | 6/2010 | Zhong et al. | |

FOREIGN PATENT DOCUMENTS

| | | |
|---|---|---|
| CN | 101643702 | 2/2010 |
| TW | 201022140 | 6/2010 |

OTHER PUBLICATIONS

Nguyen-Vu, T.D.B. et al., Vertically Aligned Carbon Nanofiber Architecture as a Multifunctional 3-D Neural Electrical Interface, IEEE Transactions on Biomedical Engineering, Jun. 2007, vol. 54, No. 6, pp. 1121-1128.*
Wei B.Q. et al., Assembly of Highly Organized Carbon Nanotube Architectures by Chemical Vapor Deposition, Chem. Mater., 2003, vol. 15, No. 8, pp. 1598-1606.*
Wang K. et al., Neural Stimulation with a Carbon Nanotube Microelectrode Array, Nano Letters, 2006, vol. 6, No. 9, pp. 2043-2048.*
Rao S.S. et al., Adhesion molecule-modified biomaterials for neural tissue engineering, Frontiers in Neuroengineering, Perspective Article, published on Jun. 9, 2009, vol. 2, article 6, pp. 1-14.*
Alder-Abramovich L. et al., Thermal and Chemical Stability of Diphenylalanine Peptide Nanotubes: Implications for Nanotechnological Applications, Langmuir, 2006, vol. 22, No. 3, pp. 1313-1320.*
Seidlits S.K. et al., Nanostructured scaffolds for neural applications, Nanomedicine, 2008, vol. 3, No. 2, pp. 183-199.*
Lacerda L. et al., Dynamic Imaging of Functionalized Multi-Walled Carbon Nanotube Systemic Circulation and Urinary Excretion, Advanced Materials, 2008, vol. 20, pp. 225-230.*
Li J. et al., Bottom-up approach for carbon nanotube interconnects, Applied Physics Letters, 2003, vol. 82, No. 15, pp. 2491-2493.*
Galvan-Garcia P. et al., Robust cell migration and neuronal growth on pristine carbon nanotube sheets and yarns, J. Biomater. Sci. Polymer. Edn., 2007, vol. 18, No. 10, pp. 1245-1261.*
Pavese M. et al., An analysis of carbon nanotube structure wettability before and after oxidation treatment, Journal of Physics: Condensed Matter, 2008, vol. 20 (474206), pp. 1-7.*
Shengnan Ge, "Laminin protein modification onto titanium oxide thin film surface and the research of dothelialization", Chinese Doctoral Dissertations & Master's Theses Full-text Datebase(master) Engineering Technology, vol. 4, Oct. 15, 2007, pp. 10-18 and 58-69.
Hua Ai et al, "Biocompatibility of layer-by-layer self-assembled nanofilm on silicone rubber for neurons", Journal of Neuroscience Methods, vol. 128, 2003, p. 8.
Jun Li et al, "Bottom-up approach for carbon nanotube interconnects", Applied Physics Letters, vol. 82,No. 15, Apr. 14, 2003, pp. 2491-2493.
Xuan Zhang et al, "Guided neurite growth on patterned carbon nanotubes", Sensors and Actuators B, vol. 106, 2005, pp. 843-850.
Weijie Huang et al, "Attaching Proteins to carbon nanotubes via Diimide-Activated Amidation", Nano Letters, vol. 2, No. 4, 2002, pp. 311-314, American.
T.D.Barbara. et al, "Vertically Aligned Carbon Nanofiber Architecture As a Multifunctional 3-D Neural Electrical Interface", IEEE Transactions on Biomedical Engineering, vol. 54, No. 6, Jun. 2007, pp. 1122,1126.
Kotaro Matsumoto et al, "Neurite Outgrowths of Neurons with Neurotrophin-Coated Carbon Nanotubes", Journal of Bioscience and Bioengineering, vol. 103,No. 3, 2007, pp. 216-220.
Zhang Tao et al.; "Water-soluble carbon nanotubes prepared by chemical modifications" Journal of Nanjing University of Technology(Natural Science Edition), vol. 32, No. 3, p. 99-104, May 31, 2010.

* cited by examiner

*Primary Examiner* — Satyendra K Singh
(74) *Attorney, Agent, or Firm* — Novak Druce Connolly Bove + Quigg LLP (57) ABSTRACT

A culture medium for growing at least one kind of cells is provided. The culture medium includes a carbon nanotube structure and a cell adhesion layer. The cell adhesion layer covers one surface of the carbon nanotube structure. The at least one kind of cells grows on the cell adhesion layer. In addition, a method for manufacturing a culture medium for growing at least one kind of cells is also provided.

6 Claims, 15 Drawing Sheets

METHOD FOR MANUFACTURING CULTURE MEDIUM COMPRISING CARBON NANOTUBES AND GROWING CELLS THEREON

This application claims all benefits accruing under 35 U.S.C. §119 from China Patent Application No. 201110097270.5, filed on Apr. 19, 2011 in the China Intellectual Property Office, disclosure of which is incorporated herein by reference.

BACKGROUND

1. Technical Field

The present disclosure relates to a culture medium and a manufacturing method thereof for growing cells.

2. Description of Related Art

Many people suffer from neurological disorders as a result of neuron injuries. Neural grafting can provide relief from these injuries. Neural grafting is a surgical transfer of tissue from various sources into specific areas of the nervous system that have been affected by injury. The neural grafting serves as a "bridge" to connect the proximate injured neurons. Grafted cells may synthesize and release growth-promoting factors near the injured neurons, thereby promoting neuron regeneration.

What is needed, therefore, is to provide a culture medium and a manufacturing method thereof to culture grafted cells to be employed in non-specific wound area.

BRIEF DESCRIPTION OF THE DRAWINGS

Many aspects of the disclosure can be better understood with reference to the drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Figure 1:
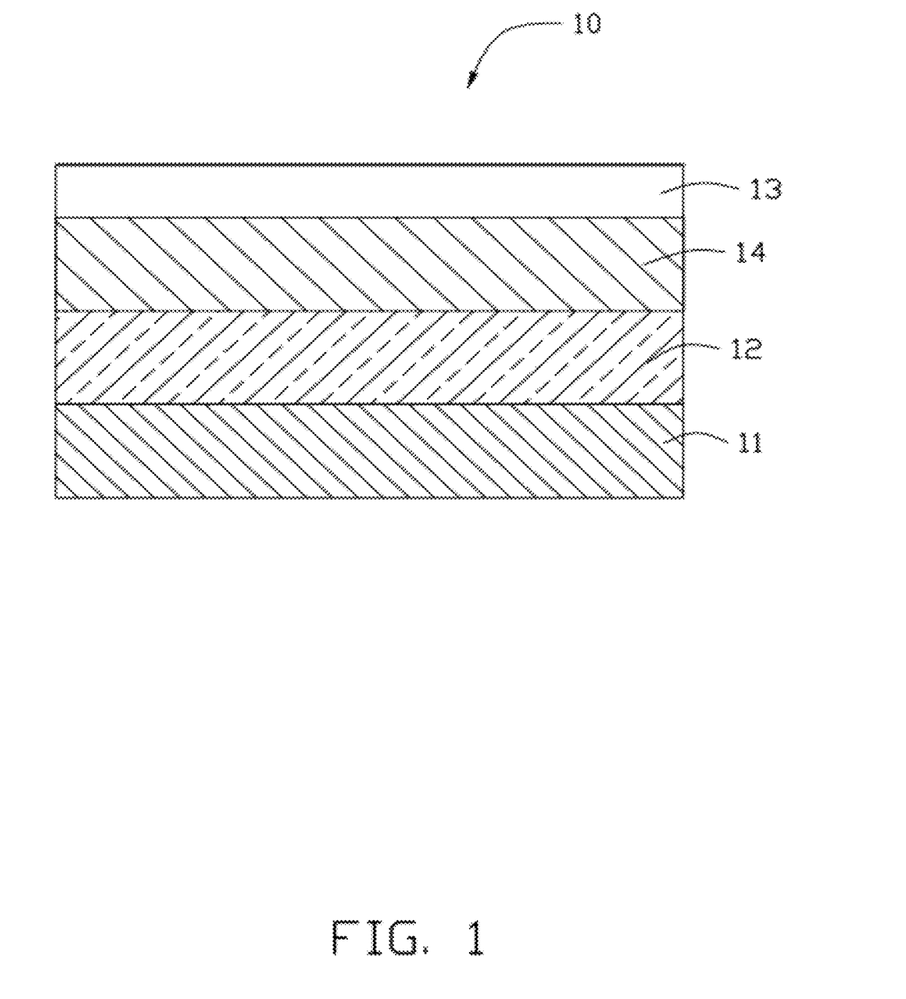
FIG. 1 is a schematic view of one embodiment of a culture medium.

Referring to FIG. 1, one embodiment of a culture medium 10 includes a substrate 11, a carbon nanotube (CNT) structure 12, and a cell adhesion layer 13. The CNT structure 12 is disposed on the substrate 11. The cell adhesion layer 13 is disposed above the CNT structure 12. In the present embodiment, the culture medium 10 is provided to grow a variety of cells and serves as a graft to be employed in the biological field. The cells of the present embodiment can be neuronal cells, skin cells, or muscle cells.

The substrate 11 is flexible or elastic. In the present embodiment, the substrate 11 is made of silicon. That is, the substrate 11 of the present embodiment is capable to bend easily without breaking. Alternatively, the substrate 11 can be composed of a flexible substrate and a silicon layer, which is disposed on the flexible substrate.

Figure 7:
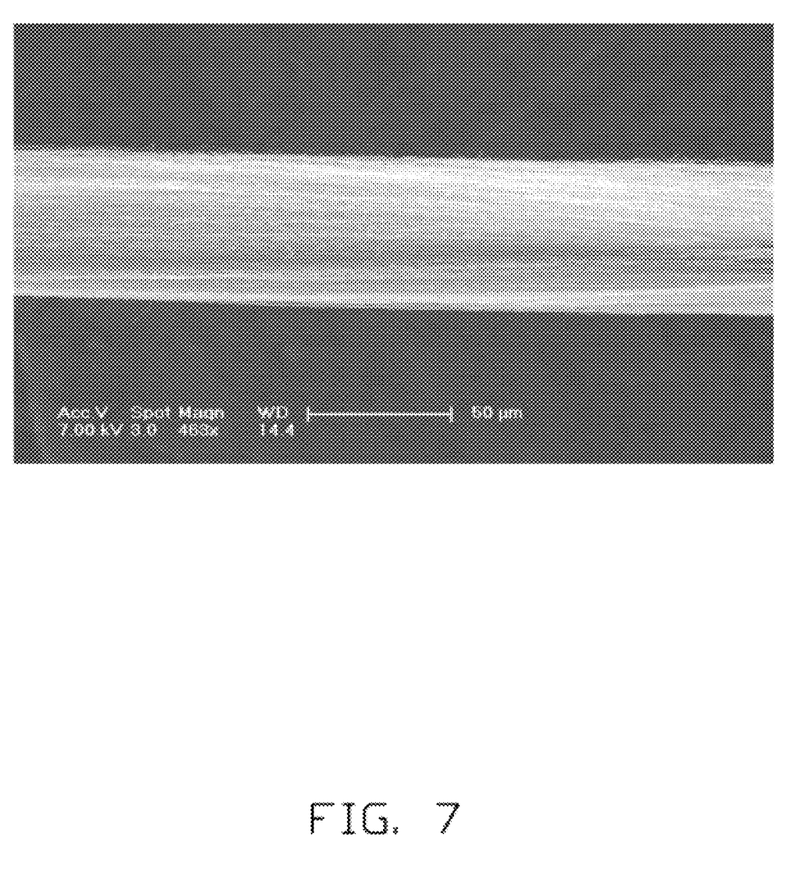
FIG. 7 is a SEM image of one embodiment of an untwisted carbon nanotube wire.
Figure 8:
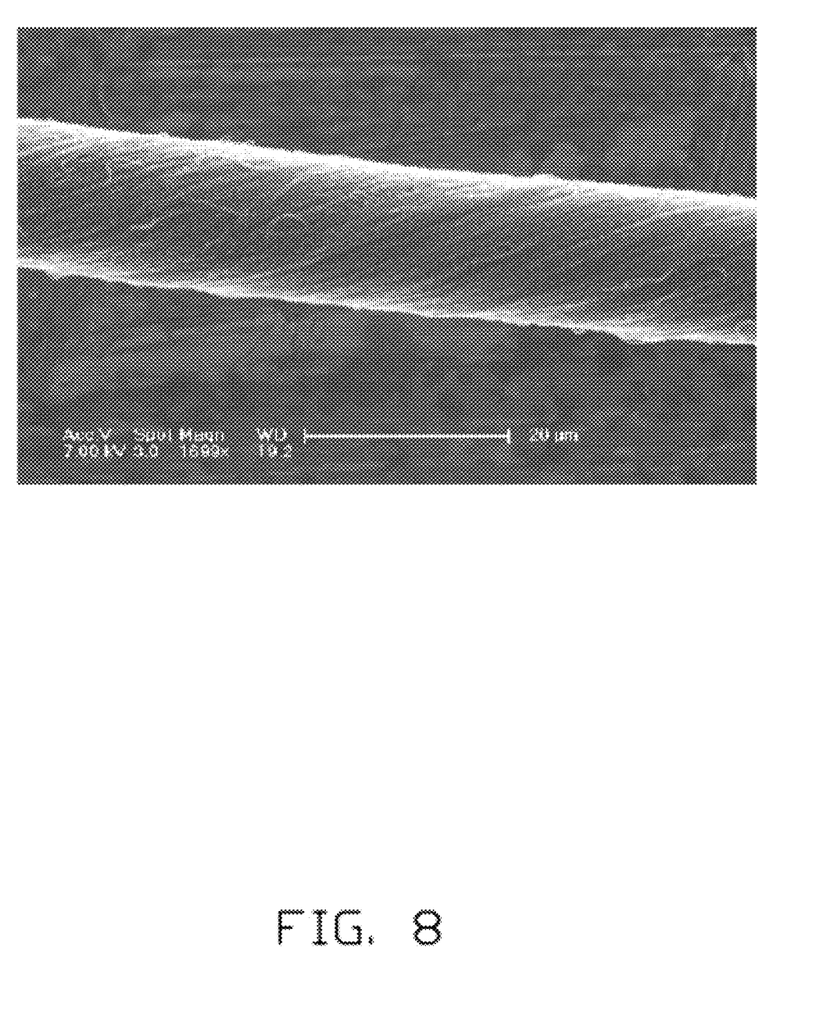
FIG. 8 is a SEM image of one embodiment of a twisted carbon nanotube wire.

The CNT structure 12 includes a plurality of carbon nanotubes to be arranged in a shape of a film or a wire. Specifically, the carbon nanotubes can be aligned to form a CNT film, as shown in FIG. 2, FIG. 3, FIG. 5, and FIG. 6 or a CNT wire, as shown in FIG. 7 and FIG. 8. Thus, at least one CNT film or a plurality of CNT wire are used to make up the CNT structures 12 of the present embodiment. Whether the CNT structure 12 is made up by CNT films or wires, the carbon nanotubes are connected by van der Waals attractive force. Consequentially, the CNT structure 12 is a free-standing structure. That is, the CNT structure 12 of the present embodiment can retain a specific shape without any supporter because of the strong connections by van der Waals attractive force between adjacent carbon nanotubes.

Figure 2:
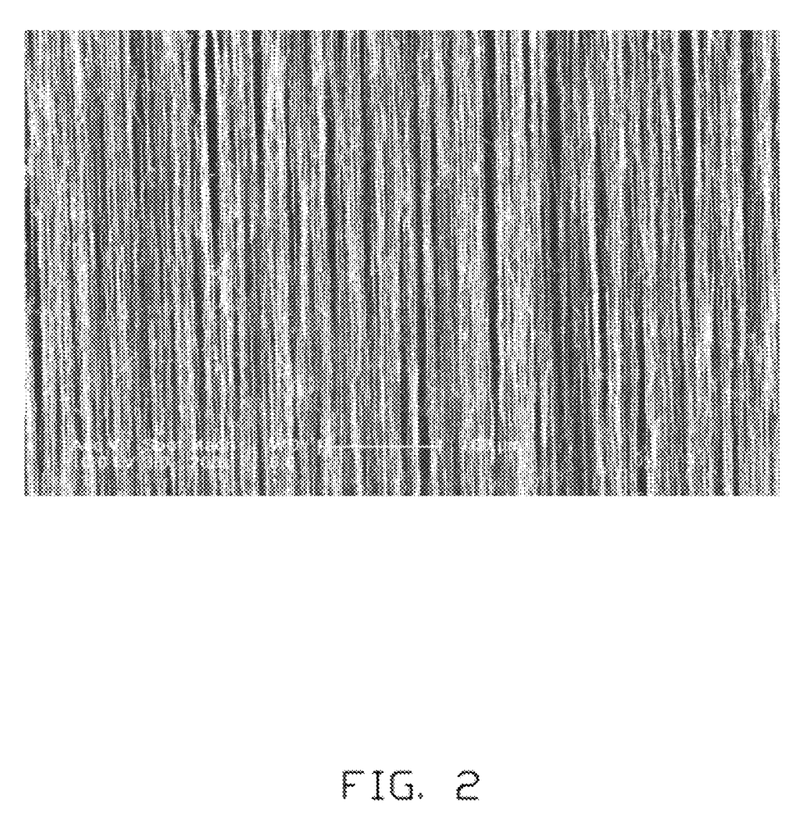
FIG. 2 is a scanning electron microscope (SEM) image of one embodiment of a drawn CNT film.

Referring to FIG. 2, the CNT film can be formed by drawing carbon nanotubes from a CNT array, which is grown on a silicon wafer by vapor deposition. Accordingly, a width of the CNT film corresponds to a size of the CNT array. In addition, the drawn carbon nanotubes are joined end to end in succession by van der Waals attractive force and are orientated substantially in the same direction. In the present embodiment, the drawn CNT film has a width ranging from about 0.1 mm to about 10 cm and has a thickness ranging from about 10 nm to about 100 μm.

Figure 3:
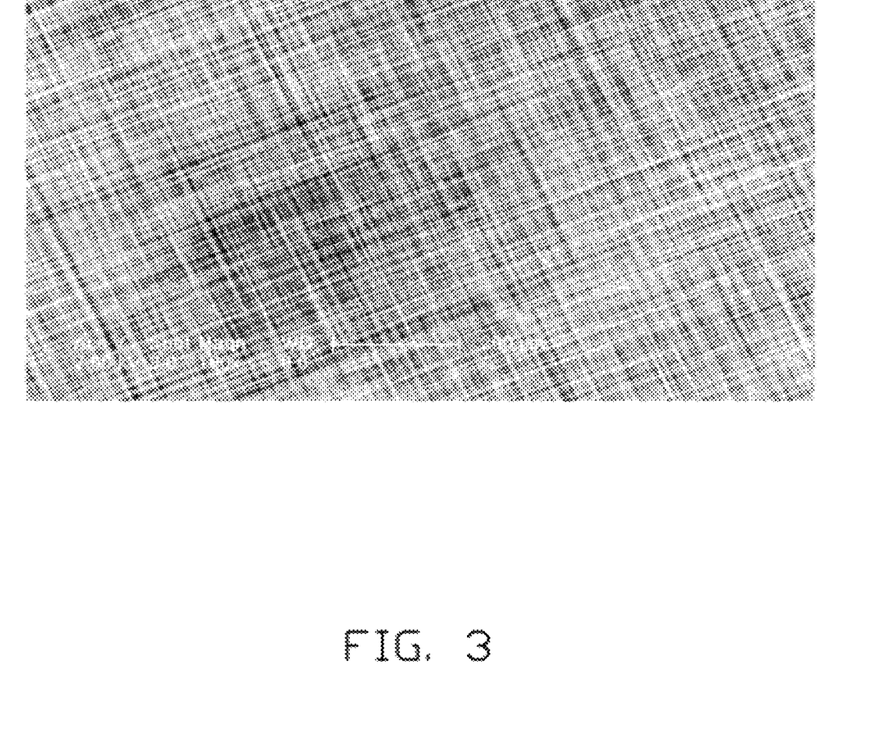
FIG. 3 is a SEM image of one embodiment of stacked CNT films.
Figure 4:
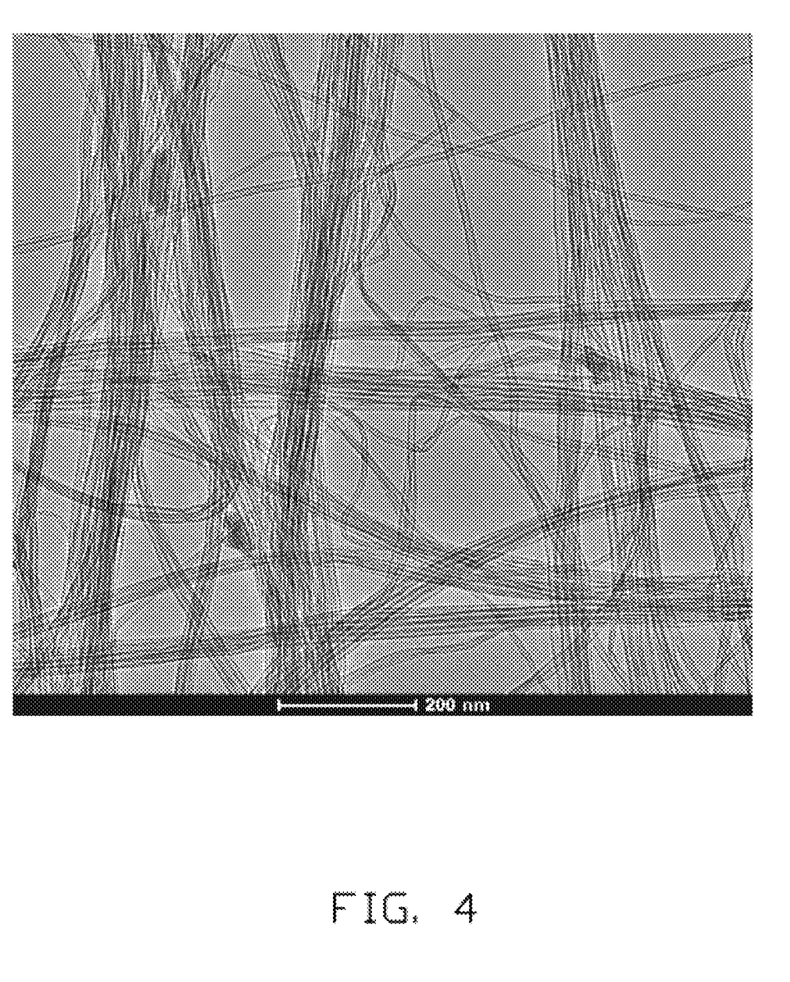
FIG. 4 is a transmission electron microscope (TEM) image of one embodiment of stacked CNT films of FIG. 3.

Referring to FIG. 3 and FIG. 4, the CNT structure 12 can include two or more CNT films that are stacked with each other on the substrate 11. The adjacent CNT films are connected to each other by van der Waals attractive force. In the present embodiment, the CNT structure 12 is formed by stacking ten or less CNT films. However, a thickness of the CNT structure 12 is arbitrary. It is understood that the thickness of the CNT structure 12 and the layers of the stacked CNT films are directly proportional.

The CNT films can be stacked in succession such that adjacent CNT films can intersect each other. In such case, an existing angle between two adjacent CNT films can be more than 0 degrees and less than or substantially equal to 90 degrees. Consequentially, the CNT films intersect to form a mesh-like structure (as shown in FIG. 4). In the present embodiment, the CNT structure 12 is comprised of ten layers of CNT films forming a mesh-like structure with carbon nanotubes intersecting substantially perpendicular to each other. The number of carbon nanotubes films and the angles made by adjacent CNT films are arbitrary and are set according to practical requirements.

Figure 5:
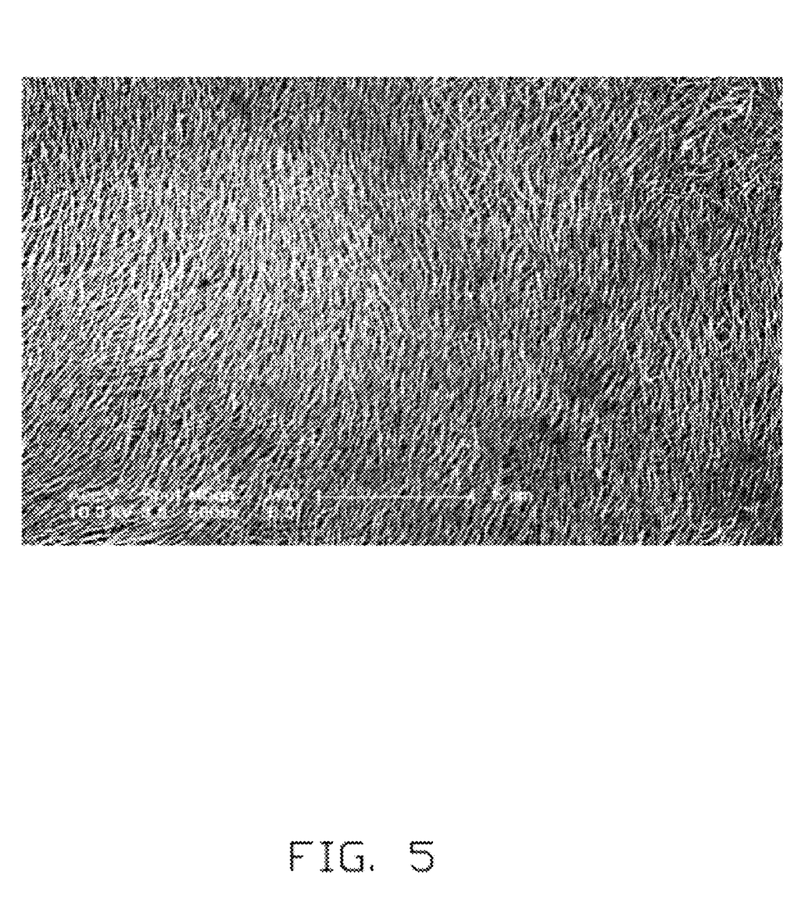
FIG. 5 is a SEM image of one embodiment of a pressed CNT film.

Referring to the FIG. 5, the CNT film can also be formed by pressing the CNT array. The carbon nanotubes of the CNT film are pressed to lay partially over each other. A plurality of micropores or interstitial spaces are defined in the pressed CNT film. A dimension of the micropore or interstitial space is in a range from about 1 nm to about 450 nm. When the carbon nanotube array is pressed along a variety of directions, the carbon nanotubes of the CNT film are oriented in different directions. When the carbon nanotube array is pressed towards one direction, the carbon nanotubes of the CNT films are primarily oriented in that one direction. The carbon nanotubes of the pressed CNT film are connected to each other by van der Waals attractive force. Thus, the CNT film can be a free-standing structure and can be bent arbitrarily for desired circumstance. Overall, an angle of the carbon nanotubes and a surface of the CNT film range from about 0 degrees to about 15 degrees. In addition, a thickness of the CNT film is closely related to the height of the carbon nanotube array, and the pressure applied to the carbon nanotube array. In the present embodiment, a thickness of the CNT film is in a range from about 0.5 nm to about 100 µm. The height of the carbon nanotube array for pressing the CNT film is more than 45 µm.

Figure 6:
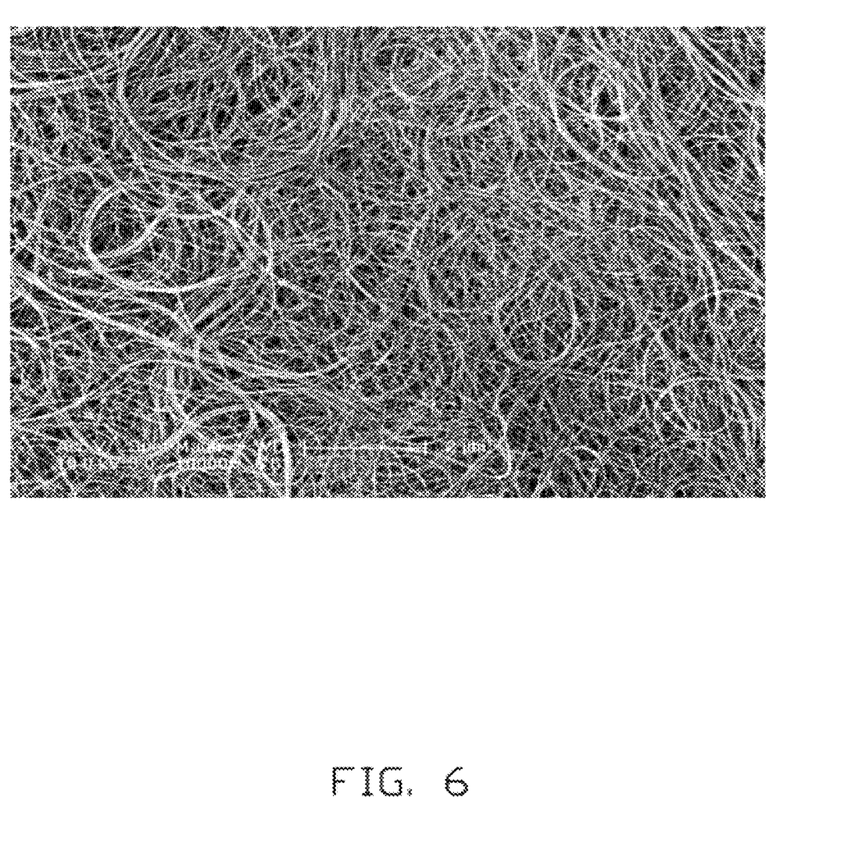
FIG. 6 is a SEM image of one embodiment of a flocculated CNT film.

Referring to FIG. 6, the CNT film can also be obtained by flocculating the carbon nanotube array. In this case, the carbon nanotubes in the CNT film are entangled by the van der Waals attractive force therebetween, thereby allowing the CNT film to form a microporous structure. That is, the CNT film is microporous and has a plurality of micropores with diameters in a range from about 1 nm to about 450 nm. In the present embodiment, a length of the carbon nanotube is more than 10 µm. Preferably, the length of carbon nanotube is in a range from about 200 µm to about 900 µm. The length of carbon nanotubes should be long enough to entangle with each other.

Referring to FIG. 7 to FIG. 8, a CNT structure 12 in accordance with another embodiment can comprise a plurality of CNT wires. Each of the CNT wires may be formed by bundling a plurality of carbon nanotubes together, as shown in FIG. 7. Accordingly, the carbon nanotubes are substantially parallel to an axis of the CNT wire to form a bundled CNT wire. The bundled CNT wire can be obtained by treating the drawn CNT film with an organic solvent, such as ethanol, methanol, acetone, dichloroethane, or chloroform. In addition, each of the CNT wires can be formed by bundling and twisting a plurality of carbon nanotubes together. Referring to FIG. 8, the carbon nanotubes are aligned helically around an axis of the CNT wire to form a twisted CNT wire. In practice, the twisted CNT wire is obtained by either twisting the bundled CNT wire or twisting the CNT film via a mechanical force. As mentioned previously, the bundled or twisted CNT wire has a diameter ranging from about 0.5 nm to about 1 mm.

The cell adhesion layer 13 covers one surface of the CNT structure 12 or opposite surfaces of the CNT structure 12. In the present embodiment, the cell adhesion layer 13 comprises a plurality of extracellular matrix proteins. For example, the extracellular matrix protein can be laminin or fibronectin, which is used to provide structural support for cell growth and regulate intercellular communication. As mentioned above, the CNT structure 12 formed by stacked CNT films, pressed CNT film, or flocculated CNT films can be a microporous or mesh-like structure. In such case, the extracellular matrix proteins can infiltrate into the interstitial spaces defined by the microporous or mesh-like structure. Therefore, the CNT structure 12 characterized by their hydrophobic nature can become hydrophilic and biocompatible. In addition, due to the flexibility and elasticity of the CNT structure 12, the culture medium 10 of the present embodiment is suitable to be employed to culture cells and serve as a graft to irregular-shaped areas.

Furthermore, referring to FIG. 1, the culture medium 10 of the present embodiment can further comprise a hydrophilic layer 14 disposed between the CNT structure 12 and the cell adhesion layer 13. The hydrophilic layer 14 comprises a variety of soluble proteins. Thus, the culture medium 10 of the present embodiment has improved hydrophilicity. In the present embodiment, a thickness of the hydrophilic layer 14 is in a range from about 0.3 µm to about 2 µm. Preferably, the hydrophilic layer 14 has a thickness of about 0.5 µm.

Figure 9:
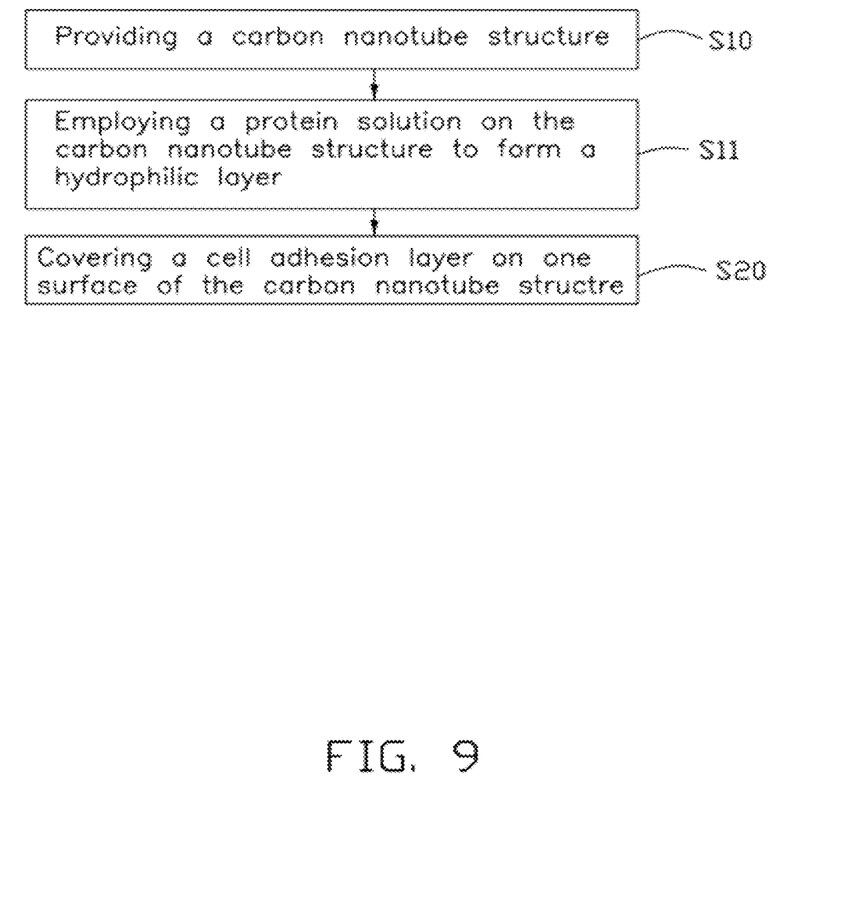
FIG. 9 shows a schematic view of a process for manufacturing the culture medium of FIG. 1.

Referring to FIG. 9, a method for manufacturing a culture medium includes providing a CNT structure and a cell adhesion layer covering on one surface of the CNT structure. In the present embodiment, the culture medium is configured to grow at least one kind of cells, such as neuronal cells, skin cells, or muscle cells. One or more cells are seeded in the culture medium.

The method is described in more detail as follows.

In step S10, the CNT structure is formed by one or more CNT films or CNT wires. Because the CNT structure is the same as described above, the detailed description is omitted here for concision. In the present embodiment, the CNT structure is sterilized by irradiating or heating the CNT structure. For example, the CNT structure can be irradiated with ultraviolet light or heated at about 120° C. to eliminate microorganisms, such as bacteria. The sterilized CNT structure is then treated with a poly-D-lysine solution. Specifically, the sterilized CNT structure is soaked in the poly-D-lysine solution. After the step of immersing the CNT structure in the poly-D-lysine solution, the poly-D-lysine coating is removed by rinsing the CNT structure with deionized water immediately. In such case, treatment of the poly-D-lysine solution will make the CNT structure to be electrically charged, enhancing the cell attachment and adhesion.

In step S20, a cell adhesion layer is formed by treating the CNT structure with an extracellular matrix protein solution. The cell adhesion layer is covered on the CNT structure. Specifically, the CNT structure can be dipped in the extracellular matrix protein solution to form the cell adhesion layer. Alternatively, the extracellular matrix protein solution can be sprayed onto the CNT structure. Forming the cell adhesion layer is not limited to the above described ways. The CNT structure becomes more hydrophilic and suitable for cellular adhesion after the treatment of the extracellular matrix protein. In the present embodiment, the extracellular matrix protein solution includes laminin with a concentration greater than or equal to 30 mg/ml.

Figure 10:
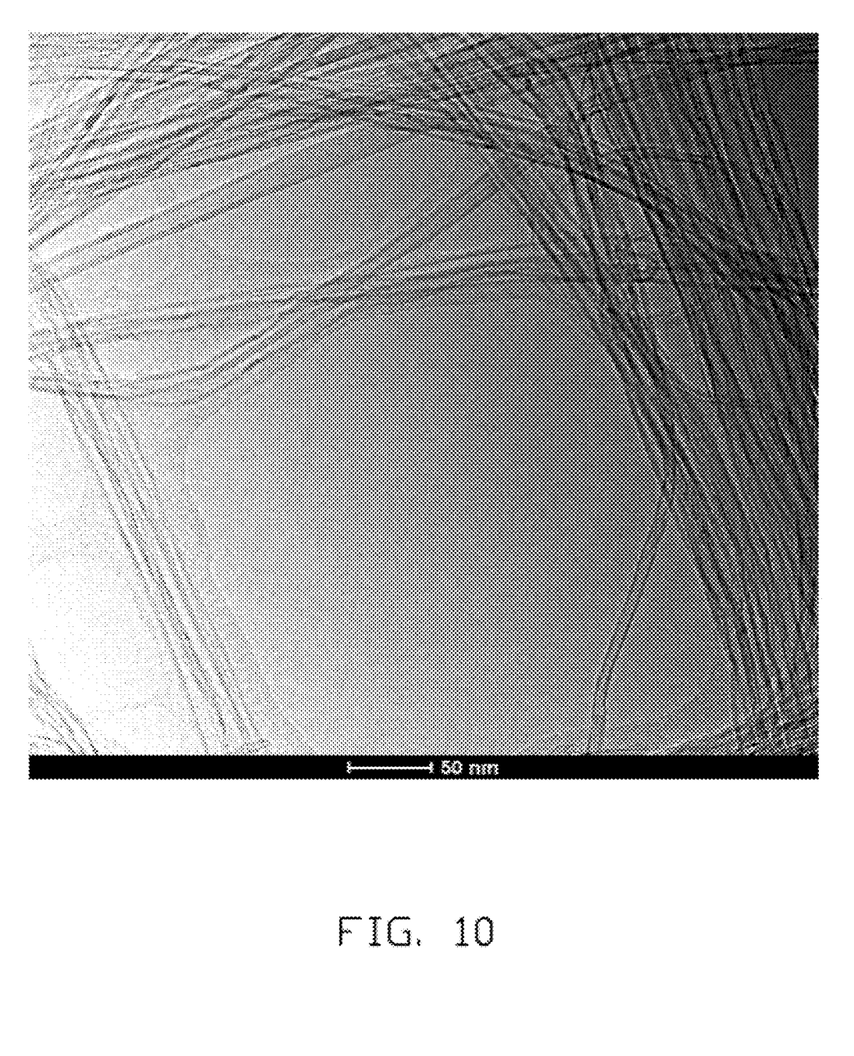
FIG. 10 is a TEM image of one embodiment of the culture medium.

In addition, the method for manufacturing a culture medium further comprises a step S11 of employing a protein solution on the CNT structure to form a hydrophilic layer, before the step S20 of covering the cell adhesion layer on the CNT structure. Referring to the FIG. 10, the CNT structure can be immersed in the protein solution for about 1.5 hours to form the hydrophilic layer on one surface of the CNT structure. After forming the hydrophilic layer, the cell adhesion layer is covered on the hydrophilic layer. In such case, the hydrophilic layer is formed between the CNT structure and the cell adhesion layer to enhance the hydrophilicity of the CNT structure. However, the way of forming the hydrophilic layer is not limited to soaking in the protein solution. Alternatively, the protein solution can be sprayed or dropped on the CNT structure. In the present embodiment, the protein solution includes soluble proteins, such as fibrous protein or plasma protein, in the biological medium, such as DMEM or RPMI. In the present embodiment, the soluble protein includes, but not limited to, bovine serum, human serum, or swine serum. In addition, the biological media is chosen according to the types of soluble proteins. Thus, the CNT structure is covered with soluble protein (e.g. fetal serum), as shown in FIG. 10.

In step S11, the CNT structure with the hydrophilic layer is also sterilized by irradiating or heating. In the present embodiment, the hydrophilic layer is irradiated for about 0.5 hours and heated at about 120° C. to avoid destroying the protein nature of the hydrophilic layer. Specifically, the CNT structure with the hydrophilic layer is heated at 120° C. for about 20 minutes.

In the present embodiment, the structural strength of the culture medium is enhanced by providing a substrate to bear the CNT structure, hydrophilic structure, and cell adhesion layer. The substrate can be made of silicon or a flexible substrate with silicon coating. The substrate can be employed in the biological field because medical grade silicone is biocompatible and durable. In addition, the substrate can be tailored to any nonspecific-shaped area because the material of silicon has excellent flexibility.

In addition, an organic solution can be dropped on the CNT structure to enhance the adhesion between the CNT structure and the substrate. As a result, the specific surface area of the CNT structure is reduced by evaporating the organic solution, and the adhesion between the CNT structure and the substrate is enhanced.

Figure 11:
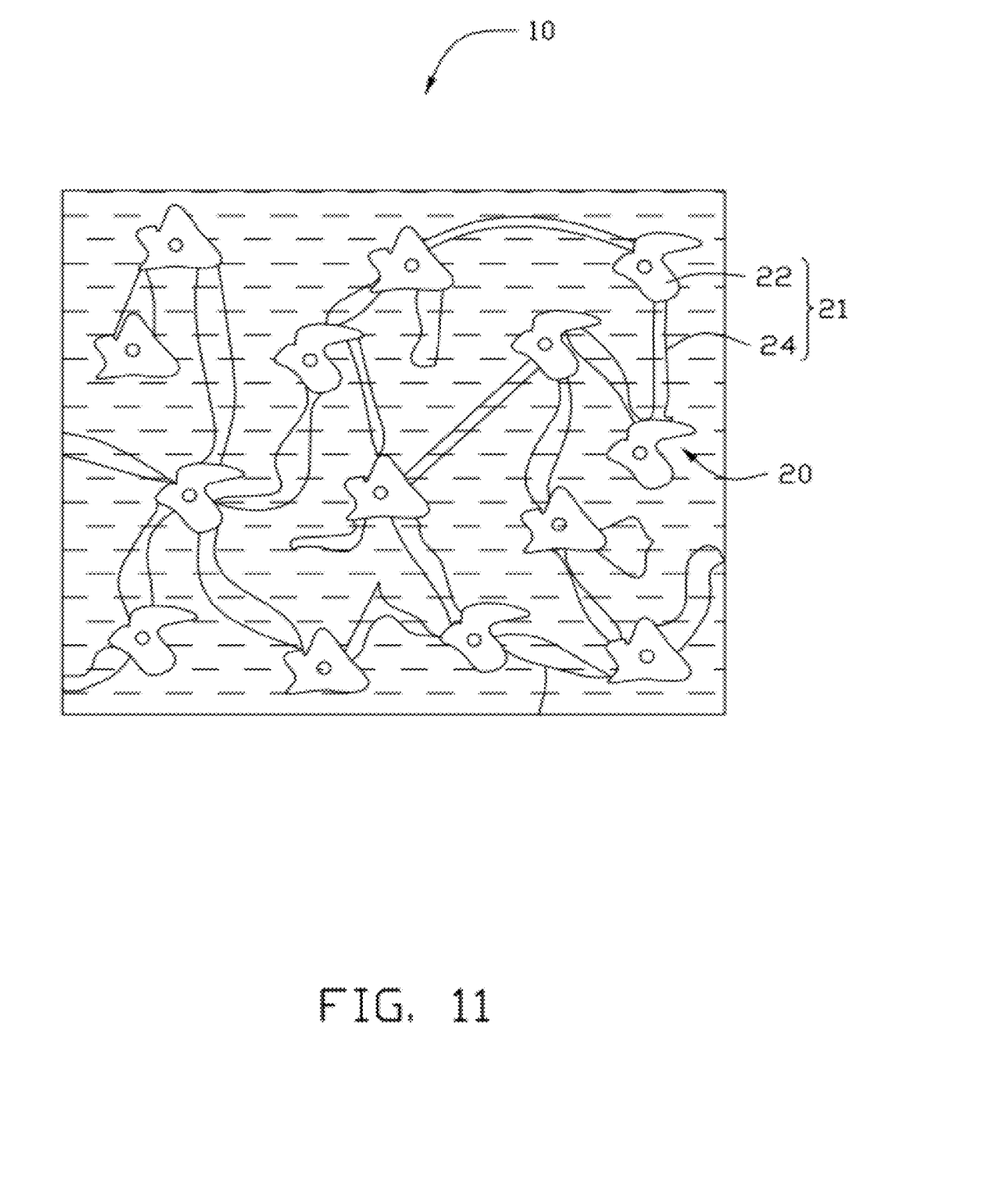
FIG. 11 is a schematic view of one embodiment of a neuronal network.
Figure 12:
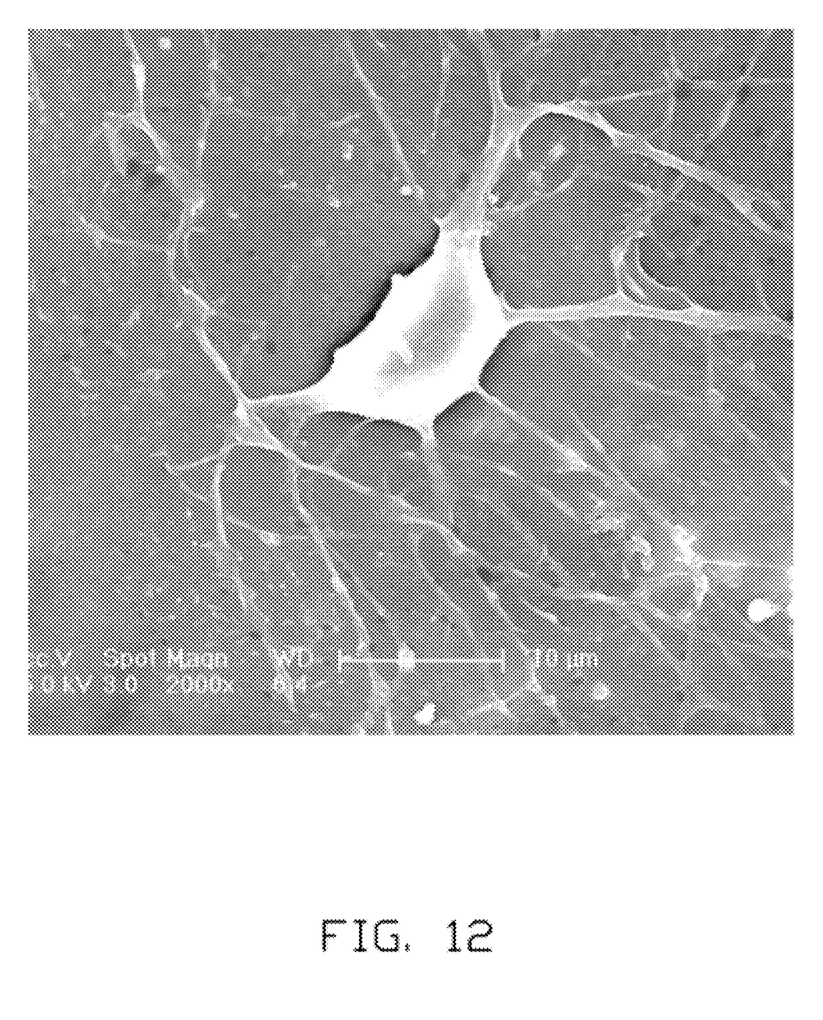
FIG. 12 and FIG. 14 are SEM images of one embodiment of differentiated neurons.
Figure 13:
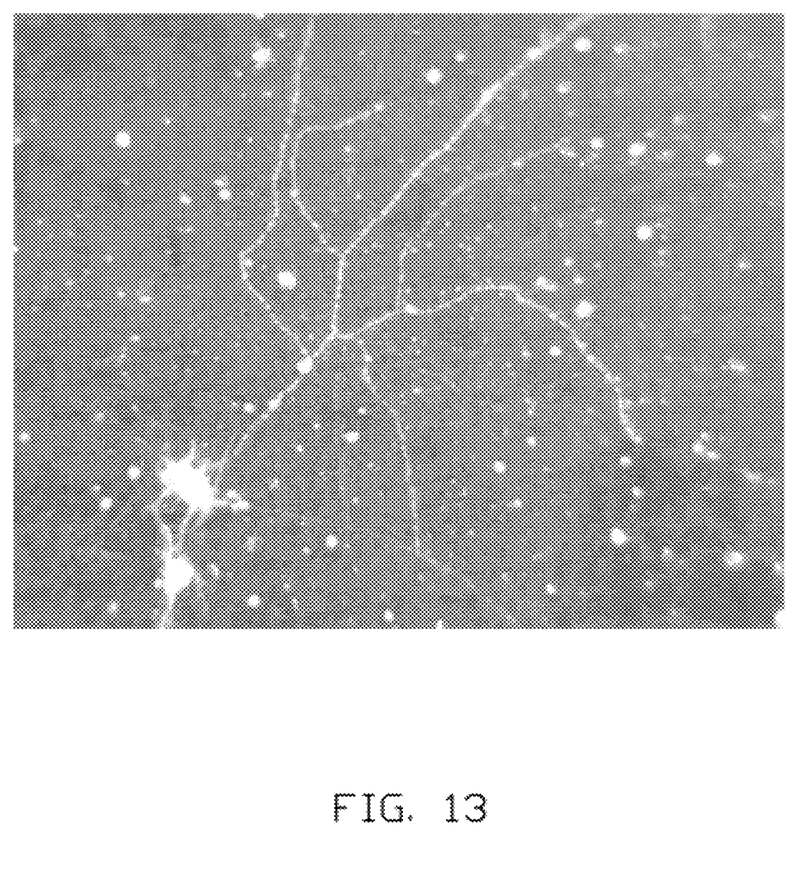
FIG. 13 and FIG. 15 are optical microscopy images of one embodiment of differentiated neurons stained with fluorescence.
Figure 14:
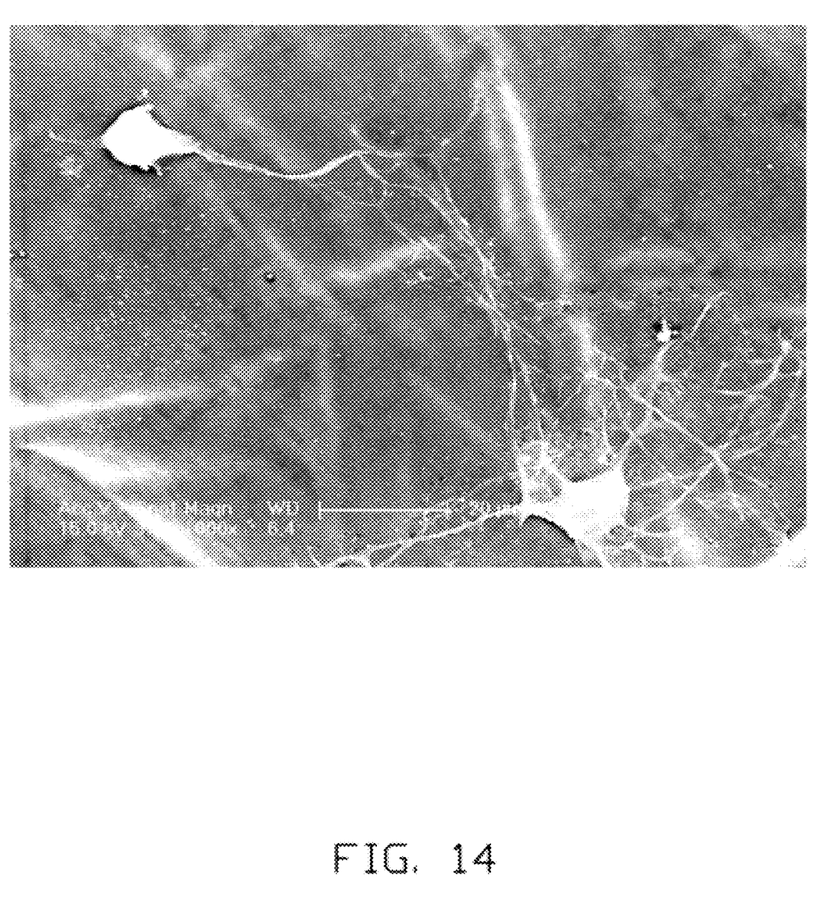
Figure 15:
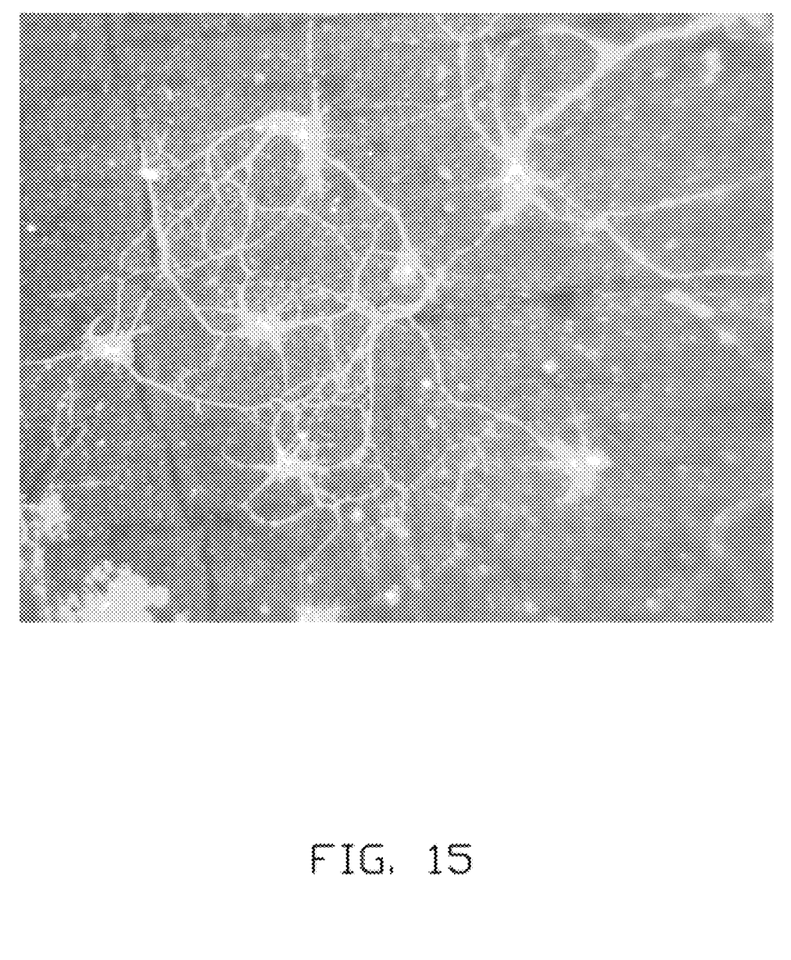

In the present embodiment, referring to FIG. 1 and FIG. 11, a variety of cells 21 can be seeded on the culture medium 10, particularly on the cell adhesion layer 13 of the culture medium 10. Neuronal cells (e.g. hippocampal neurons) are taken as an example. The culture medium 10 can be placed in the cell culture dish to culture the cells 21. It is noted the cell growth factor chosen according to the type of cells 21 to be cultured is necessary to nourish cells growth and differentiate a variety of cell types. In the present embodiment, the hippocampal neurons on the culture medium 10 are incubated in an incubator with a $CO_2$ concentration of about 5% and a temperature of about 37° C. During the optimal culture period, the individual neuron cells 21 will branch a plurality of neuritis 24 from a cell body 22 towards and connect with adjacent neurons to form a neuronal network 20 (as shown in FIG. 11, FIG. 12, FIG. 13). Thus, the neuronal communication can be propagated. Referring to FIG. 14 and FIG. 15, the neurons on the culture medium of the present embodiment are connected to each other after incubating for about 15 days.

In the present embodiment, due to the flexibility of CNT structure, the culture medium can be tailored arbitrarily and employed to cure an area with any shape. In addition, the cell adhesion layer 13 provides an environment for cell adhesion and cell growth. Thus, the culture medium of the present embodiment can be served as a graft and have a wide range of applications in the biological field.

It is to be understood that the above-described embodiments are intended to illustrate rather than limit the disclosure. Any elements described in accordance with any embodiments is understood that they can be used in addition or substituted in other embodiments. Embodiments can also be used together. Variations may be made to the embodiments without departing from the spirit of the disclosure. The above-described embodiments illustrate the scope of the disclosure but do not restrict the scope of the disclosure.

Depending on the embodiment, certain of the steps of methods described may be removed, others may be added, and the sequence of steps may be altered. It is also to be understood that the description and the claims drawn to a method may include some indication in reference to certain steps. However, the indication used is only to be viewed for identification purposes and not as a suggestion as to an order for the steps.

What is claimed is:

1. A method for manufacturing a culture medium and culturing cells thereon, comprising:
   (1) making a carbon nanotube structure comprising at least one free-standing carbon nanotube film having a plurality of pressed carbon nanotubes;
   (2) sterilizing the carbon nanotube structure;
   (3) applying a poly-D-lysine solution on the sterilized carbon nanotube structure;
   (4) removing the poly-D-lysine solution from the carbon nanotube structure by rinsing the carbon nanotube structure immediately with deionized water;
   (5) placing the poly-D-lysine treated carbon nanotube structure on a first surface of a substrate, wherein the substrate comprises silicon or a coating of silicon, and wherein an angle of the plurality of pressed carbon nanotubes and the first surface is about 15 degrees and a thickness of said carbon nanotube film is in the range of from about 0.5 nm to about 100 μm;
   (6) forming a cell adhesion layer directly on a surface of the poly-D-lysine treated carbon nanotube structure from step (5) by soaking said carbon nanotube structure in a solution comprising an extracellular matrix protein; and
   (7) seeding and growing at least one kind of cells on the cell adhesion layer.

2. The method of claim 1, wherein the step of forming the cell adhesion layer comprises soaking the carbon nanotube structure in a solution comprising fibronectin.

3. The method of claim 1, wherein the step of sterilizing the carbon nanotube structure comprises:
   irradiating the carbon nanotube structure with ultraviolet light; and
   treating the carbon nanotube structure with heat.

4. A method for manufacturing a culture medium and culturing cells thereon, comprising:
   (1) making a carbon nanotube structure comprising at least one free-standing carbon nanotube film having a plurality of pressed carbon nanotubes;
   (2) sterilizing the carbon nanotube structure;
   (3) applying a poly-D-lysine solution on the sterilized carbon nanotube structure;
   (4) removing the poly-D-lysine solution from the carbon nanotube structure by rinsing the carbon nanotube structure immediately with deionized water;
   (5) placing the poly-D-lysine treated carbon nanotube structure on a first surface of a substrate, wherein the substrate comprises silicon or a coating of silicon, and wherein an angle of the plurality of pressed carbon nanotubes and the first surface is about 15 degrees and a thickness of said carbon nanotube film is in the range of from about 0.5 nm to about 100 μm;
   (6) forming a hydrophilic layer directly on a surface of the poly-D-lysine treated carbon nanotube structure from step (5) by applying a solution comprising serum on the carbon nanotube structure;
   (7) forming a cell adhesion layer directly on a surface of the hydrophilic layer by soaking said carbon nanotube structure obtained from step (6) in a solution comprising an extracellular matrix protein; and
   (8) seeding and growing at least one kind of cells on the cell adhesion layer.

5. The method of claim 4, wherein the substrate is flexible.

6. The method of claim 4, wherein a thickness of the hydrophilic layer is in a range from about 0.3 μm to about 2 μm.

* * * * *